United States Patent [19]

Suddendorf et al.

[11] 4,206,160

[45] Jun. 3, 1980

[54] MECHANICAL DEVICE TO PRODUCE A FINELY DISPERSED AEROSOL

[75] Inventors: Ronald F. Suddendorf; Kenneth W. Boyer, both of Springfield, Va.

[73] Assignee: The United States of America as represented by the Department of Health, Education and Welfare, Washington, D.C.

[21] Appl. No.: 945,131

[22] Filed: Sep. 25, 1978

[51] Int. Cl.$^2$ ............................................. B01F 3/04
[52] U.S. Cl. ............................ 261/78 A; 128/200.14; 239/338; 239/426; 239/434; 261/DIG. 65
[58] Field of Search ................... 261/78 A, 118, 112, 261/DIG. 65; 128/193, 194; 239/8, 337, 338, 426, 434

[56] References Cited

U.S. PATENT DOCUMENTS

| | | |
|---|---|---|
| 2,906,513 | 9/1959 | Tabor ............................. 261/78 A |
| 3,249,553 | 5/1966 | Steinberg ..................... 261/78 A X |
| 3,421,692 | 1/1969 | Babington et al. ...................... 239/8 |
| 3,421,699 | 1/1969 | Babington et al. .................. 239/337 |
| 3,473,530 | 10/1969 | Urbanowicz ......................... 128/194 |
| 3,606,159 | 9/1971 | Sutton ......................... 261/78 A X |
| 3,857,909 | 12/1974 | Huggins ........................ 128/194 X |
| 3,864,326 | 2/1975 | Babington ..................... 239/338 X |
| 3,944,635 | 3/1976 | Siegenthaler .................. 261/78 A X |
| 4,007,238 | 2/1977 | Glenn ................................. 261/78 A |

*Primary Examiner*—Richard L. Chiesa
*Attorney, Agent, or Firm*—Browdy and Neimark

[57] ABSTRACT

A nebulizer to produce a finely dispersed aerosol from a solution passing over its surface comprises a chamber through which a gas, such as air, is adapted to be blown. The chamber has an outlet conduit, and mounted in the chamber facing the outlet conduit is an inclined upright bar formed with a longitudinal V-groove having a central gas exit port to which is connected a gas input delivery tube. A sample introduction tube is connected to the top end of the bar at said V-groove to admit sample solution thereto. The side walls of the V-groove below the gas exit port are lower in height than above the gas exit port to prevent aerosol droplets from settling on the walls and from interfering with the entry of the aerosol into the exit port. An impactor rod is adjustably mounted on the lower portion of the bar and is adjusted so that its top end is in front of the gas exit port. A protective cover is provided on the upper portion of the bar, above the gas exit port, and prevents aerosol droplets from settling on the bar and from again flowing over the gas exit port.

15 Claims, 5 Drawing Figures

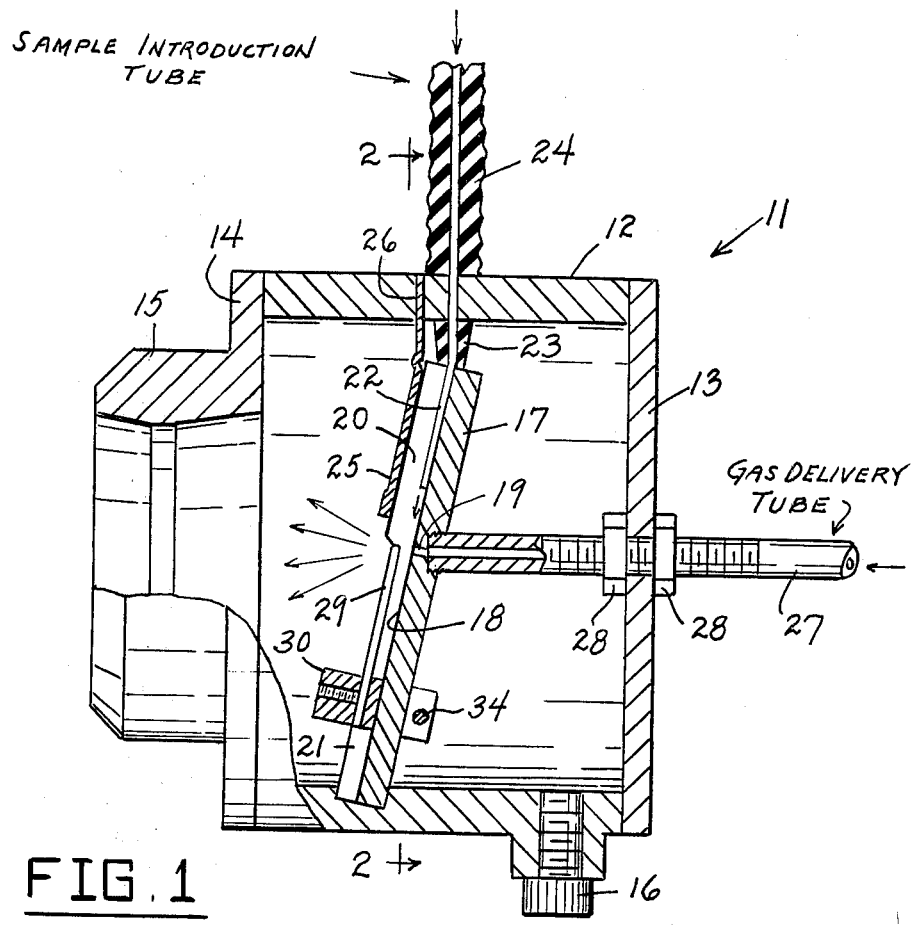
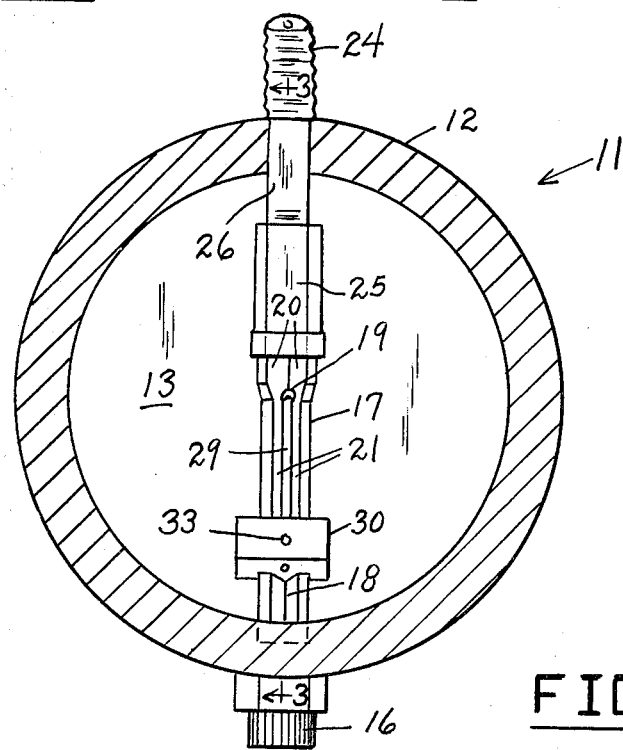
FIG. 1
FIG. 2

MECHANICAL DEVICE TO PRODUCE A FINELY DISPERSED AEROSOL

FIELD OF THE INVENTION

This invention relates to diffusing liquids in gaseous media, and more particularly to an apparatus for diffusing a sample liquid in a carrier gas to form a finely dispersed aerosol suitable for analysis of the contents of the sample liquid by inductively coupled plasma apparatus or similar analyzing equipment.

BACKGROUND OF THE INVENTION

The current trend toward multielement analysis has been accelerated by the availability of the inductively coupled plasma apparatus (ICP). However, most analytical procedures employing the ICP require that the sample be made available in the form of a solution for introduction by a nebulizer into the ICP as a finely dispersed aerosol. One of the major problems of the ICP has been the absence of a totally satisfactory nebulizing device, especially for solutions that have a high salt content.

Sample introduction devices for direct analysis of solutions with the inductively coupled argon plasma ICP apparatus must meet two general requirements. First, the nebulizer must conveniently produce a stable generation of aerosol, and second, the aerosol must be produced with an argon flow rate compatible with the ICP. The argon may serve as both the source of the aerosol generating force and the carrier gas for the aerosol, as occurs with conventional pneumatic nebulizers, or it may serve as the carrier gas only, as with ultrasonic nebulizers. In either case, its flow rate must be approximately one liter/min to be compatible with most commercially available ICPs.

Because of the restraint placed on the argon flow rate, nebulizers commonly used in atomic absorption or flame emission with a higher flow rate of aspirating gas will not operate at optimum efficiency, and thus will not produce a sufficient quantity of aerosol to be of value with the ICP. For this reason, several new nebulizer designs have appeared which are capable of efficient aerosol production at low gas flow rates.

Two of the most popular types currently in use are the crossflow (1) and the concentric glass (2) nebulizers. Both devices rely on capillary tubes in their design to generate aerosol, using low flow rates of argon gas. Although these nebulizers are capable of efficient aerosol generation, it is possible for the capillary tubes to become partially or completely clogged, especially when analyzing high salt content samples. Thus, they require frequent cleaning to restore the original rate of aerosol generation, or necessitate restandardization of the ICP.

Several designs based on ultrasonic nebulization have been reported for use with the ICP (3,4,5,6,7). One of the advantages of ultrasonic nebulizers is the absence of restricted capillary tubes for sample introduction. As a result, instability due to clogging is eliminated. However, a serious disadvantage resides in the inconvenient and time-consuming sample changing procedure, along with the requirement of electronics to drive the piezoelectric transducer. A more recent design (8) has improved the sample changing procedure with ultrasonic nebulizers.

Fritted disc nebulizers (9) are also being investigated as sample introduction devices for the ICP. Like ultrasonic nebulizers, the fritted disc nebulizer does not require the solution to pass through restricted capillary tubes for aerosol generation. At the present time, relatively little data is available documenting the use of this nebulizer with the ICP.

Application of the Babington nebulizer for analysis of high salt content samples by flame atomic absorption analysis has been reported (10). The nubulizer was designed for atomic absorption, and as such operates using a gas flow of from 9 to 12 liters/min, far in excess of the one liter/min flow rate suitable for use with the ICP.

In the above discussion, reference has been made to the following publications:

1. R. N. Kniseley, H. Amenson, C. C. Butler and V. A. Fassel, *Applied Spectrosc.* 28, 285(1974)

2. J. E. Meinhard Associates Catalog 1976, P.O. Box 9, Tustin, CA 92680.

3. R. H. Wendt and V. A. Fassel, *Anal. Chem.* 37. 920 (1965).

4. H. C. Hoare and R. A. Mostyn, *Anal. Chem.* 39, 1153(1967).

5. V. A. Fassel and G. W. Dickinson, *Anal. Chem.* 40, 247(1968).

6. J. M. Mermet and J. P. Robin, *Anal. Chem.* 40, 1918(1968).

7. G. W. Dickinson and V. A. Fassel, *Anal. Chem.* 41, 1021(1969).

8. K. W. Olsen, W. J. Haas and V. A. Fassel, *Anal. Chem* 49, 632(1977).

9. C. T. Apel, T. M. Bieniewsky, L. E. Cox and D. W. Steinhaus, *ICP Information Newsletter* 3, 1(1977).

10. R. C. Fry and M. B. Denton, *Anal, Chem.* 49, 1413(1977).

In addition, a preliminary search in connection with the present invention yielded the following prior U.S. Pat. Nos. of interest: Tabor, 2,906,513; Babington et al, 3,421,692; Babington et al, 3,421,699; Urbanowicz, 3,473,530; Huggins, 3,857,909; Babington, 3,864,326; Glenn, 4,007,238.

SUMMARY OF THE INVENTION

Accordingly, an object of the present invention is to provide for improved generation of fine aerosols which overcomes the disadvantages and deficiencies of the previously employed nebulizer devices.

A further object of the invention is to provide an improved nebulizer for aerosol generation which is mechanically simple in construction, which is suitable for use with inductively coupled plasma (ICP) analytical apparatus, which is capable of continuous operation without clogging, and which is free from drift commonly associated with the use of nebulizers of the capillary bore pneumatic type.

A still further object of the invention is to provide an improved nebulizer for aerosol generation which possesses rapid cleanout and convenient sample changing capabilities.

A still further object of the invention is to provide an improved nebulizer for aerosol generation suitable for use with inductively coupled plasma analytical apparatus which introduces more sample to the plasma than the crossflow nebulizer and which can provide a larger signal and improved detection limits as compared to those obtained with the crossflow nebulizer.

A still further object of the invention is to provide an improved nebulizer for aerosol generation which employs a base having a V-shaped configuration, whereby the sample solution comes in contact with a larger surface area, which employs an adjustable gas impactor rod which can be readily adjusted for optimum performance, which does not require exact positioning of the liquid sample admission tube to maintain satisfactory performance, and which requires a relatively short cleanout time to make it substantially free of memory effects.

BRIEF DESCRIPTION OF THE DRAWINGS

Further objects and advantages of the invention will become apparent from the following description and claims, and from the accompanying drawings, wherein:

FIG. 1 is a side elevational view, partly in vertical cross-section, of an improved nebulizer constructed in accordance with the present invention.

FIG. 2 is a transverse vertical cross-sectional view taken substantially on line 2—2 of FIG. 1.

DESCRIPTION OF A PREFERRED EMBODIMENT

Figure 3:
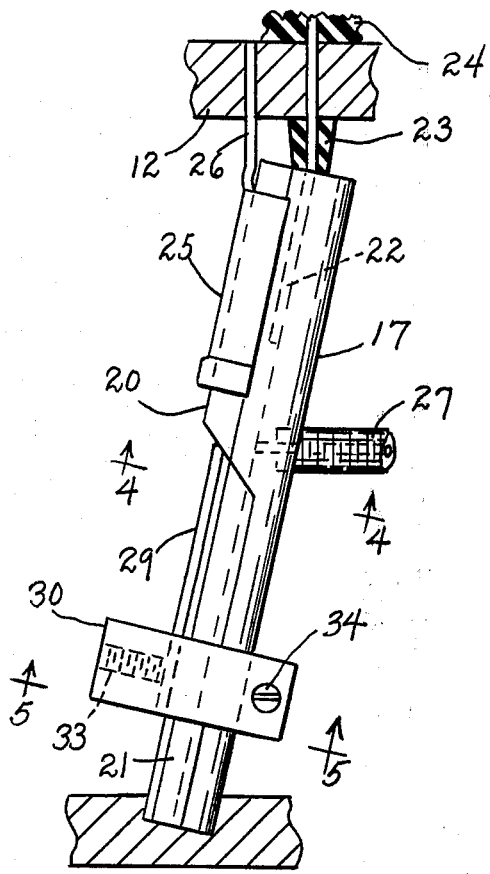
FIG. 3 is an enlarged fragmentary vertical cross-sectional view taken substantially on the line 3—3 of FIG. 2, showing the nebulizer base assembly in side elevation.
Figure 4:
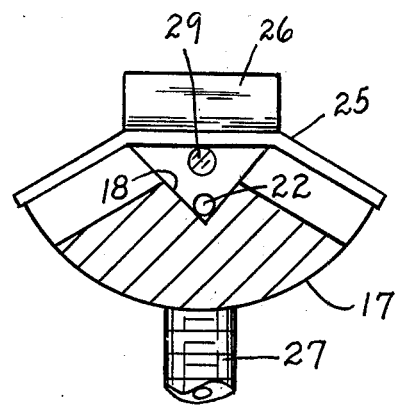
FIG. 4 is an enlarged cross-sectional view taken substantially on the line 4—4 of FIG. 3.
Figure 5:
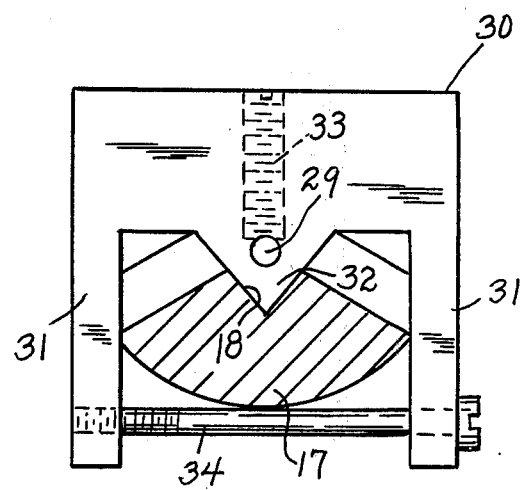
FIG. 5 is an enlarged cross-sectional view taken substantially on the line 5—5 of FIG. 3.

Referring to the drawings, a nebulizer 11 according to the present invention comprises a generally cylindrical housing 12 of suitable sturdy material, such as metal or plastic, e.g. Plexiglas, having a circular rear wall 13 and an annular front wall 14 integrally formed with an aerosol discharge conduit 15. Housing 12 is provided at its rear portion with a removable bottom drain plug 16.

Mounted in the housing chamber is a nebulizer base assembly comprising an elongated upright base member 17 which is inclined to the vertical, as viewed in FIG. 1, wherein the nebulizer is shown in its normal orientation, namely, with its axis horizontal. Base member 17 is formed with a longitudinal V-shaped groove 18 which faces the discharge conduit 15 and which is in communication with a gas exit port 19 formed at the intermediate portion of the base member, extending substantially perpendicular to the bottom of the groove 18. The walls 20,20 of the groove above the gas exit port 19 are of substantially greater height than the walls 21,21 of the groove below said exit port. Making the walls 21,21 of lower height than the walls 20,20 prevents aerosol droplets from settling on the walls and reflowing over the gas exit port 19, as will be presently explained, thereby preventing the occurrence of pulsations in the production of aerosol.

A sample introduction tube 22, formed, for example, of stainless steel and lined with inert plastic such as Teflon, is centered in and touches the V-shaped groove 18 near the top of the base member 17, extending through a bushing 23 and the housing wall and being suitably connected to a flexible sample admission conduit 24.

The upper portion of base member 17 and the portion of tube 22 contained therein are covered by a protective cover 25 which extends from just above the gas exit port 19 to the top of the base member. Cover 25 is provided with a supporting tab 26 which extends into and is suitably secured in the adjacent housing wall, as shown in FIG. 1. The protective cover 25 serves to prevent aerosol droplets from settling on the base member 17 or the sample introduction tube 22 and again flowing over the gas exit port 19. Such an occurrence would produce undesired pulsations in the rate of aerosol production.

Pressurized carrier gas, such as argon, nitrogen or air, is delivered to the nebulizer via a gas delivery tube 27 extending centrally through the rear wall 13 and clampingly secured thereto by opposing clamping nuts 28,28. The inner end of tube 27 is suitably rigidly secured to base member 17 in communication with the exit port 19, as by being threadedly engaged in said base member. A glass impactor rod 29 is adjustably mounted with its top end in front of the gas exit port 19. The rod 29 is clamped in a mounting yoke 30, which is in turn clampingly engaged on the lower portion of base member 17. For example, as shown in FIG. 5, the yoke 30 may be generally U-shaped to closely receive the lower portion of base member 17 between the opposing, somewhat resilient, yoke arms 31,31, and the yoke may have a depending triangular lug 32 slidably engaged in the V-groove 18. A clamping bolt 34 extends through the free end portions of arms 31,31, close to or in engagement with the bottom surface of base member 17, as viewed in FIG. 5, and threadedly engaged with one of the arms 31. The impactor rod 29 is received in a bore in the lug 32 and is clamped therein by a set screw 33. The rod 29 is thus supported parallel to the V-groove 18 and the position of its rounded top end may be accurately adjusted so as to be suitably centered relative to the jet of nebulizing gas emerging from the gas exit port 19.

In a typical embodiment, the base member 17 was of gold-plated stainless steel and was 5 cm long and 8 mm wide. The gas exit port 19 was 0.23 mm in diameter. The side walls of the groove 18 from the gas exit port 19 to the top of the base member were 2 mm high and were 1 mm high below the gas exit port. The impactor rod mounting yoke 30 was of gold-plated aluminum. The protective cover 25 was likewise of gold-plated aluminum.

In operation, the sample liquid is pumped through the sample introduction tube 22, for example, by a conventional peristaltic pump, onto the surface of the V-groove 18 above the gas exit port 19. The V-groove 18 causes the liquid, under the influence of gravity, to flow in a stream over the gas exit port. This causes breakup of the liquid stream by the exciting gas and results in the formation of a dense and fine aerosol. Larger drops formed by this process are forced against the impactor rod rounded tip and are further broken up. The gas used to generate the aerosol also serves as the carrier gas to deliver the aerosol via the discharge conduit 15 to the plasma.

Typical experiments performed with the above-described nebulizer 11 used an ICP consisting of a Jarrell Ash Model 975 Plasma Atom Comp (made by Jarrell Ash Co., 590 Lincoln St., Waltham, Mass. 02154) direct reading spectrometric system with dynamic background correction, capable of the simultaneous determination of 25 elements. Data handling was accomplished with the aid of a PDP-8 minicomputer. Forward power to the plasma was maintained at 1100 W., with reflected power less than 2 W. Argon flow through the nebulizer was one liter/min. Efficiency of the above-described nebulizer was found to be adequate, although somewhat less than that of a crossflow nebulizer, but with a much higher sample uptake rate, resulting in more aerosol being produced.

In operation, although the above-described V-groove nebulizer 11 produces a signal slightly noisier than that obtained with the crossflow nebulizer, it introduces more sample to the plasma, which results in a larger signal, and in detection limits comparable to those obtained with the crossflow nebulizer. (A "detection limit" was defined as the concentration required to produce a signal twice the standard deviation of the background. All detection limits were determined with the element of interest in distilled deionized water.)

Also, in operation sample solution comes into contact with a large surface area of the nebulizer base member 17. Consequently, undesirable memory effects might be expected to occur with this nebulizer. To investigate this, a blank solution was analyzed, followed by the constant nebulization for 15 minutes of a solution containing 10 μg/ml of 10 selected elements. At the end of 15 minutes, the blank solution was run for 90 seconds and then again analyzed. It was found that the 90 second cleanout time was adequate to return the blank reading to its original value and that no memory effect exists under these conditions.

An additional advantage of the V-groove nebulizer above described is the simplicity of the adjustments needed to obtain optimum performance. Whereas exact positioning of capillary tubes is required with the crossflow nebulizer, the only requirement with respect to the sample introduction tube 22 of the above-described nebulizer 11 is that it should lie in the groove 18 of the base member 17. A small misalignment of the sample tube will not affect performance, as the sample solution is forced to flow over the gas exit port 19 in the same fashion each time by the V-shaped groove 18 in the nebulizer base member.

While a specific embodiment of an improved nebulizer has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A nebulizer comprising a chamber having a substantially horizontally directed aerosol outlet, an upright generally vertically disposed elongated bar member mounted in said chamber and having a longitudinal groove of generally V-shaped cross-section open at its wide part therein with the wide part of the groove facing said outlet, said bar member being formed at its intermediate portion with a horizontal gas exit port communicating with the apex of said groove, means to deliver gas under pressure through said gas exit port and toward said aerosol outlet, means to introduce to said groove a liquid sample, said means including a liquid sample introduction tube disposed in the upper portion of said groove above said gas exit port for feeding liquid down said groove, impactor means located in front of and spaced from said gas exit port, and liquid sample conduit means communicatively connected to said sample introduction tube.

2. The nebulizer of claim 1, and wherein the side walls of the groove portion above said gas exit port are of greater height than the side walls of the groove portion below said gas exit port.

3. The nebulizer of claim 1, wherein said impactor means comprises an impactor element mounted on said bar member and having an end located in front of and spaced from said gas exit port.

4. The nebulizer of claim 3, and wherein the side walls of the portion of the groove above said gas exit port are of greater height than the side walls of the portion of the groove below said gas exit port.

5. The nebulizer of claim 4, and a cover member mounted on the portion of the bar member above said gas exit port and overlying said groove.

6. The nebulizer of claim 5, and wherein said sample introduction tube is in longitudinal surface contact with the bottom portion of the groove.

7. The nebulizer of claim 1, and yoke means adjustably mounted on the portion of the bar member below said gas exit port, said impactor means comprising an impactor rod secured on said yoke means and extending parallel to said groove, with its top end located in front of and spaced from said gas exit port.

8. The nebulizer of claim 7, and wherein the height of the side walls of the groove portion above said gas exit port is greater than the height of the side walls of the groove portion below said gas exit port.

9. The nebulizer of claim 8, and wherein said sample introduction tube is in longitudinal surface contact with the bottom of the groove.

10. The nebulizer of claim 9, and a cover member mounted on the upper portion of the bar member overlying the portion of the groove above said gas exit port.

11. A nebulizer comprising a chamber having a substantially laterally directed aerosol outlet conduit, an upright elongated bar member mounted in said chamber and having a longitudinal groove facing said outlet conduit, said bar member being formed at its intermediate portion with a gas exit port communicating with said groove generally perpendicularly thereto, a gas delivery conduit communicatively connected to said gas exit port, a liquid sample introduction tube longitudinally disposed in the upper portion of said groove above said gas exit port to deliver liquid down said groove, said sample introduction tube being in surface contact longitudinally with the bottom of said groove, and liquid sample conduit means communicatively connected to said sample introduction tube.

12. A nebulizer in accordance with claim 11, wherein said groove is substantially V-shaped in cross section.

13. A nebulizer comprising a chamber having a substantially laterally directed aerosol outlet conduit, an upright elongated bar member mounted in said chamber and having a longitudinal substantially V-shaped groove facing said outlet conduit, said bar member being formed at its intermediate portion with a gas exit port communicating with said groove generally perpendicularly thereto, a gas delivery conduit communicatively connected to said gas exit port, a liquid sample introduction tube longitudinally disposed in the upper portion of said groove above said gas exit port, said sample introduction tube being in surface contact longitudinally with the bottom portion of said groove whereby liquid sample flows down said V-shaped groove, and liquid sample conduit means communicatively connected to said sample introduction tube.

14. A nebulizer comprising a chamber having a substantially laterally directed aerosol outlet conduit, an upright elongated bar member mounted in said chamber and having a longitudinal groove facing said outlet conduit, said bar member being formed at its intermediate portion with a gas exit port communicating with said groove generally perpendicularly thereto, a gas delivery conduit communicatively connected to said gas exit port, a liquid sample introduction tube longitudinally disposed in the upper portion of said groove above said gas exit port, said bar member being inclined to the vertical and said liquid sample introduction tube being in surface contact longitudinally with the bottom of said groove whereby liquid sample flows down said groove, and liquid sample conduit means communicatively connected to said sample introduction tube.

15. The nebulizer of claim 14, and a cover member mounted on and overlying the portion of said bar member above said gas exit port.

* * * * *